United States Patent
Wang et al.

(10) Patent No.: US 11,156,582 B2
(45) Date of Patent: Oct. 26, 2021

(54) SYSTEMS FOR DETECTING AND QUANTIFYING NUCLEIC ACIDS

(71) Applicants: Georgia State University Research Foundation, Inc., Atlanta, GA (US); The United States Government as Represented by the Department of Veterans Affairs, Washington, DC (US)

(72) Inventors: Gangli Wang, Brookhaven, GA (US); Tanyu Wang, Atlanta, GA (US); Didier Merlin, Decatur, GA (US)

(73) Assignees: GEORGIA STATE RESEARCH FOUNDATION, INC., Atlanta, GA (US); THE UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 479 days.

(21) Appl. No.: 15/741,553

(22) PCT Filed: Jul. 6, 2016

(86) PCT No.: PCT/US2016/041150
§ 371 (c)(1),
(2) Date: Jan. 3, 2018

(87) PCT Pub. No.: WO2017/007826
PCT Pub. Date: Jan. 12, 2017

(65) Prior Publication Data
US 2018/0195996 A1 Jul. 12, 2018

Related U.S. Application Data

(60) Provisional application No. 62/189,144, filed on Jul. 6, 2015, provisional application No. 62/194,125, filed on Jul. 17, 2015.

(51) Int. Cl.
*G01N 27/416* (2006.01)
*C12Q 1/68* (2018.01)
(Continued)

(52) U.S. Cl.
CPC .............. *G01N 27/416* (2013.01); *C12Q 1/68* (2013.01); *C12Q 1/682* (2013.01); *C12Q 1/6886* (2013.01);
(Continued)

(58) Field of Classification Search
CPC ................ C12Q 1/6825; C12Q 1/6816; C12Q 2563/113; C12Q 2600/178; C12Q 1/68;
(Continued)

(56) References Cited

U.S. PATENT DOCUMENTS

2004/0197801 A1   10/2004   Liu et al.
2010/0133118 A1*  6/2010   Sosnowski ........... C12Q 1/6825
                                             205/777.5

FOREIGN PATENT DOCUMENTS

WO        20100060060        5/2010

OTHER PUBLICATIONS

Labib et al. Anal Chem, 2013, 85, 9422-9427. (Year: 2013).*
Xia et al. Analytica Chimica Acta 878 (2015) 95-101 (Year: 2015).*
Loaiza et al. (Sensors 2005, 5, 344-363). (Year: 2005).*
Extended European Search Report dated Jan. 25, 2019.
Hung et al., "MicroRNAs in Hepatocellular Carcinoma: Carcinogenesis, Progression, and Therapeutic Target," BioMed. Research International, pp. 1-11, 2014.
(Continued)

*Primary Examiner* — Sally A Merkling
(74) *Attorney, Agent, or Firm* — Pabst Patent Group LLP

(57) ABSTRACT

This invention is based, in part, on our discovery of an essentially one-step, label-free system comprising a sensing unit having a redox current reporter and a nucleic acid sequence complementary to that of a target nucleic acid of interest or sufficiently complementary to that of the target nucleic acid or a sequence therein to specifically bind the target nucleic acid. The sensing unit is bound to an electroconductive substrate (e.g., a carbon- or metal-containing microelectrode (e.g., a gold microelectrode)), and the system
(Continued)

includes a signal amplification mechanism that does not rely upon a redox enzyme and thereby overcomes a fundamental limitation of microelectrode DNA sensors that fail to generate detectable current in the presence of only small amounts of a target nucleic acid.

19 Claims, 5 Drawing Sheets

Specification includes a Sequence Listing.

(51) Int. Cl.
    *G01N 27/48*     (2006.01)
    *C12Q 1/6886*     (2018.01)
    *C12Q 1/682*     (2018.01)

(52) U.S. Cl.
    CPC ....... *G01N 27/48* (2013.01); *C12Q 2600/158* (2013.01); *C12Q 2600/178* (2013.01); *G01N 2800/00* (2013.01)

(58) Field of Classification Search
    CPC   C12Q 1/6886; C12Q 1/682; C12Q 2600/158; G01N 27/3275; G01N 27/3276; G01N 33/542; G01N 33/54353; G01N 27/416; G01N 27/48; G01N 2800/00; B01J 2219/00605; B01J 2219/00653; B01J 2219/00722; A61B 5/14735
See application file for complete search history.

(56) References Cited

OTHER PUBLICATIONS

International Search Report for PCT/US16/41150, dated Oct. 6, 2016 (4 pages).
Lautner et al., "Electrochemical Detection of miRNAs," Electroanalysis, 26:1-12, 2014.
Pei, et al., "A DNA Nanostructure-based Biomolecular Probe Carrier Platform for Electrochemical Biosensing," Advanced Materials, 22(42):4754-4758, 2010.
Pheeney, et al., "DNA Electrochemistry with Tethered Methylene Blue," Langmuir, 28(17)7063-7070, 2012.
Yi Xiao, et al. "An Electrochemical Sensor for Single Nucleotide Polymorphism Detection in Serum Based on a Triple-Stem DNA Probe", J. Am. Chem. Soc., 131(42):15311-15316, 2009.
Gao et al., "Detection of MicroRNAs Using Electrocatalytic Nanoparticle Tags", *Analytical Chemistry*, 7(5):1470-1477 (2006). Abstract Only.
Labib et al., "Protein Electrocatalysis for Direct Sensing of Circulating MicroRNAs", *Analytical Chemistry*, 87(2):1395-1403 (2014).
Labib et al., "Four-Way Junction Formation Promoting Ultrasensitive Electrochemical Detection of MicroRNA", *Analytical Chemistry*, 85(20):9422-9427 (2013).
Xia et al., "An electrochemical microRNAs biosensor with the signal amplification of alkaline phosphates and electrochemical-cehmical-chemical redox cycling", *Analytica Chimica Acta*, 878:95-101 (2015).
Extended European Search Report dated Jan. 9, 2019.

* cited by examiner

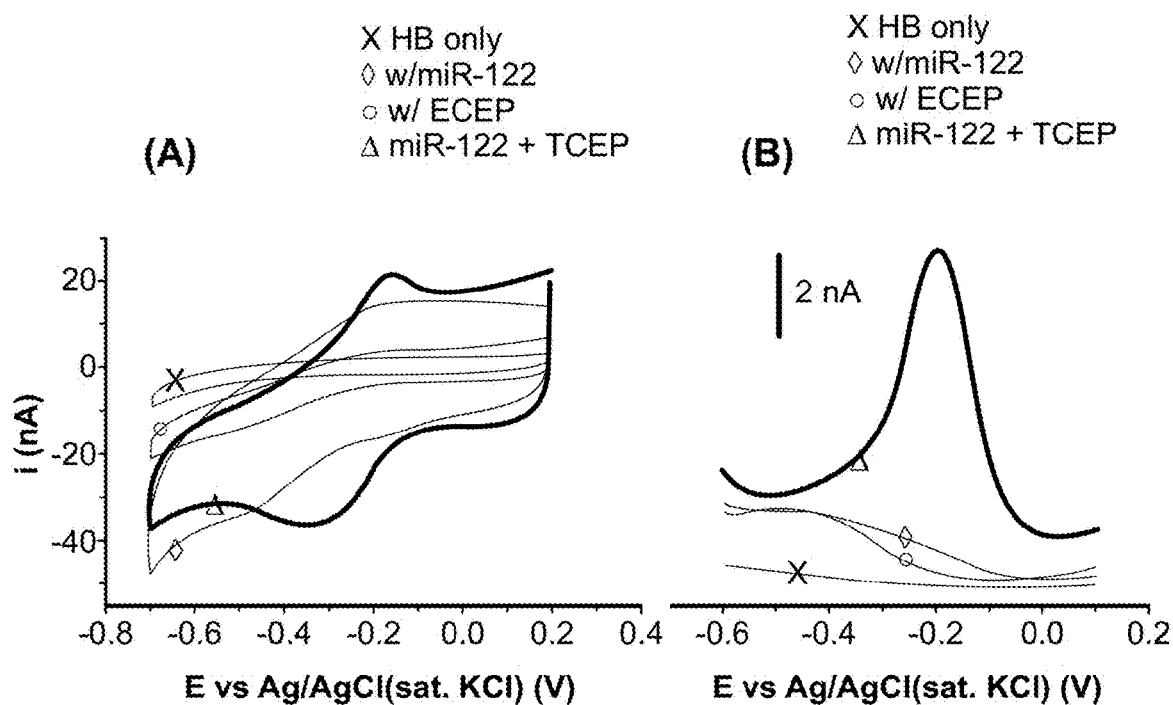
FIG. 3A
FIG. 3B
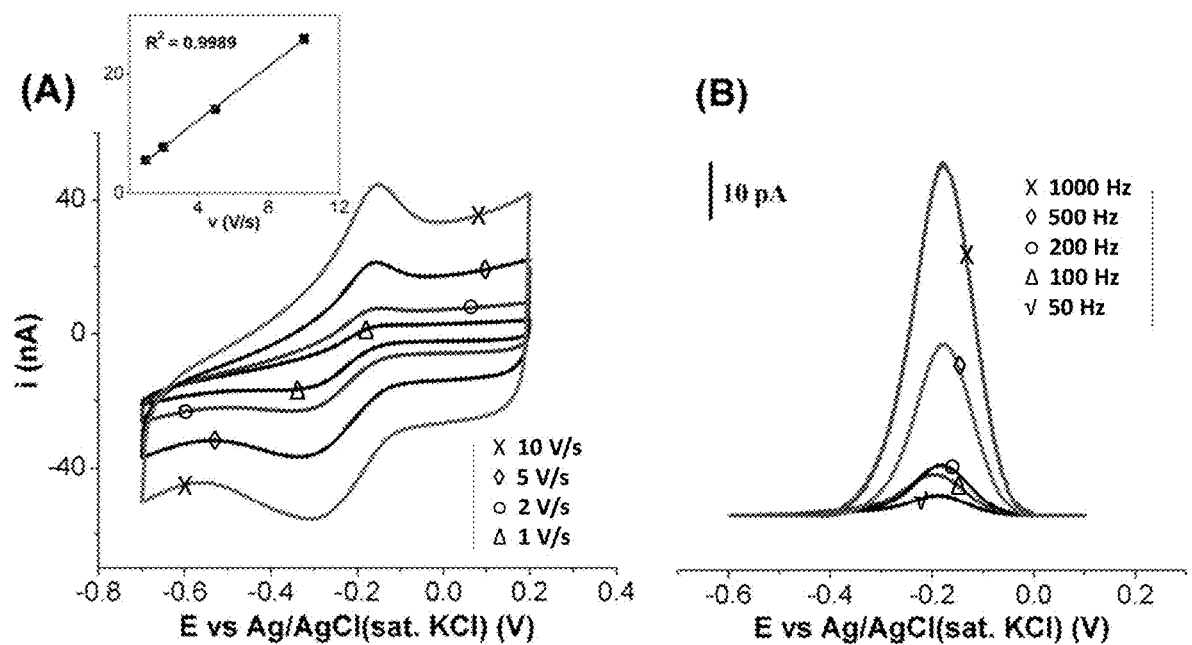
FIG. 4A
FIG. 4B

SEQUENCE LISTING

<160> NUMBER OF SEQ ID NOS: 4

<210> SEQ ID NO 1
<211> LENGTH: 69
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
ggagtgtttt ttttcgtgtt tgttttttca aacaccattg tcacactcca tttttttttt        60
ttgacaatg                                                                69

<210> SEQ ID NO 2
<211> LENGTH: 22
<212> TYPE: RNA
<213> ORGANISM: Mus musculus

<400> SEQUENCE: 2
uggaguguga caauguguu ug                                                  22

<210> SEQ ID NO 3
<211> LENGTH: 18
<212> TYPE: RNA
<213> ORGANISM: Mus musculus

<400> SEQUENCE: 3
agugugauaa uggcguuu                                                      18

<210> SEQ ID NO 4
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 4
uggaguguga uaauggcguu ug                                          22
```

SYSTEMS FOR DETECTING AND QUANTIFYING NUCLEIC ACIDS

CROSS-REFERENCE TO RELATED APPLICATIONS

This application is a U.S. National Stage Application of International Application No. PCT/US2016/041150, filed Jul. 6, 2016, which claims the benefit of the filing date of U.S. Provisional Application No. 62/189,144, filed Jul. 6, 2015, and U.S. Provisional Application No. 62/194,125, filed Jul. 17, 2015. The content of each of the above-referenced prior applications is hereby incorporated herein by reference in its entirety.

STATEMENT REGARDING FEDERALLY SPONSORED RESEARCH

This invention was made with government support under grants RO1-DK-071594 and RO1-DK-064711 awarded by the National Institutes of Health. The government has certain rights in the invention.

REFERENCE TO SEQUENCE LISTING

The Sequence Listing submitted on Jul. 26, 2021, as a text file named "GSURF_2015_14_ST25.txt" created on Jul. 22, 2021, and having a size of 1,216 bytes is hereby incorporated by reference pursuant to 37 C.F.R. § 1.52(e)(5).

FIELD OF THE INVENTION

This invention relates generally to systems for detecting and/or quantitating target nucleic acids (particularly small RNAs such as miRNAs). The systems comprise a plurality of sensing units, each of which includes a sequence-specific nucleic acid and a redox current reporter. The sensing units are bound to an electroconductive substrate and exposed to a solution including chemical reactants that function as either reductants or oxidants. When the sequence-specific nucleic acid in the sensing unit anneals to a target nucleic acid in a sample that is made available to the system (e.g., by being added to the solution surrounding the sensing units), the redox current reporter is freed from its previously contained position and can then repetitively react with the substrate and with the chemical reactants (via either reduction or oxidation). This amplifies the current flowing between the redox current reporter and the substrate, thereby allowing detection of target nucleic acids even when those nucleic acids are present at very low levels in a sample.

BACKGROUND

MicroRNAs (miRNAs) are a class of single-strand, short, endogenous non-protein-coding RNAs with approximately 19-23 nucleotides (Dong et al., *Chem. Rev.*, 113:6207, 2013). In recent years, increasing evidence has indicated that miRNAs play important roles in a wide range of physiological processes, and their aberrant expressions are associated with various diseases (Lewis et al. *Cell,* 120:15, 2005; Cullen, *Nature,* 457:421, 2009; Laterza et al., *Clin. Chem.,* 55:1977, 2009). Unlike most RNAs that are prone to degradation, recent reports suggest that a stable population of miRNAs exist in circulation (Wang et al., *Proc. Natl. Acad. Sci. USA,* 106:4402, 2009). Therefore, miRNA expression and quantitative profiles can be employed as biomarkers for the onset and progression of disease states (Chen et al., *Cell Res.,* 18:997, 2008; Kosaka et al., *Cancer Sci.,* 101:2087, 2010). However, the detection of miRNAs faces major challenges due to their unique characteristics, including low abundance and sequence similarity among family members (Michel et al., *Exp. Biol. Med.* 231:490, 2006; Klein, *Trends Mol. Med.,* 8:257, 2002; Lim, *Genes Dev.,* 17:991, 2003; Liang et al., *BMC Genomics,* 8:166, 2007).

Capable methods or sensors featuring fast, low-cost detection with suitable sensitivity and selectivity for broad applications remain to be established (Dong et al., *Chem. Rev.,* 113:6207, 2013; Lautner and Gyurcsányi, *Electroanalysis,* 26:1224, 2014). Quantitative reverse transcription polymerase chain reaction (qRT-PCR) and microarray are the mainstream techniques for identification and quantitation of circulating miRNAs in plasma or serum (Lee et al., *Chem. Int. Ed.,* 50:12487, 2011; Liu et al., *Proc. Natl. Acad. Sci. USA,* 101:9740, 2004; Thomson et al., *Nat. Methods,* 1:47, 2004). Although microarray is a high throughput analysis platform, the sensitivity is not suitable for low-level miRNA quantitation (Liu et al., *Proc. Natl. Acad. Sci. USA,* 101:9740, 2004; Lodes et al., *PLoS One,* 4:e6229, 2009). The qRT-PCR is almost the unanimous choice for quantifying miRNAs due to its high sensitivity, but the methodology suffers from time-consuming multi-step analysis process and requires highly skilled personnel working in a lab environment (Asaga et al., *Clin. Chem.,* 57:84, 2011; Zhi et al., *PLoS One,* 8:e56718, 2013; Gaur et al., *Cancer Res.,* 67:2456, 2007; Zhang et al., *J. Chem. Commun.,* 47:9465, 2011). Moreover, most qRT-PCR analysis determines relative miRNA abundance (with respect to an often-not-validated reference miRNA) in biological samples which makes quantitative, point-of-care miRNA analysis not possible. Thus, there is an urgent need to directly obtain absolute concentrations or quantities of miRNAs and broadly other nucleic acids. Further, the complicated procedures and high cost also prevent application in many clinical and in-home or point-of-care applications. For more efficient detection of miRNAs with high sensitivity and selectivity, electrochemical sensors, among many others, have been developed to complement current methods and provide additional information as parallel analysis (Gao and Yu, *Biosens. Bioelectron.,* 22:933, 2007; Gao and Yu, *Sens. Actuators,* 121:552, 2007; Gao and Peng, *Biosens. Bioelectron.,* 26:3768, 2011; Gao, *Analyst,* 137:1674, 2012; Labib et al., *J. Am. Chem. Soc.,* 135:3027, 2013; Labib et al., *Anal. Chem.,* 85:9422, 2013; Labib et al., *Anal. Chem.,* 87:1395, 2015). Particularly, the employment of DNA-/aptamer-based recognition coupled with electrochemical detection has become a popular method to develop rapid and quantitative folding-based sensors (Labib et al., *J. Am. Chem. Soc.,* 135:3027, 2013; Labib et al., *Anal. Chem.,* 85:9422, 2013; Labib et al., *Anal. Chem.,* 87:1395, 2015; Wang et al., *Anal. Chem.,* 84:6400, 2012; Pohlmann and Sprinzl, *Anal. Chem.,* 82:4434, 2010; Hu et al., *J. Am. Chem. Soc.,* 134:7066, 2012). Further improvements in those promising sensors are needed to establish them as alternative methods complimenting or replacing qRT-PCR analysis.

The incorporation of micro- and nanoelectrodes in sensor fabrication has further pushed electrochemical sensing into new domains of space and time (Salamifar and Lai, *Anal. Chem.,* 86:2849, 2014; Liu et al., *Anal. Chem.,* 86:11417, 2014). The miniaturized detection platform is meritorious for analysis of samples with limited quantity/volume at high throughput. A small-scale electrode offers unique properties such as high mass-transfer rate, small RC constants, and faster electrochemical responses (Salamifar and Lai, *Anal. Chem.,* 86:2849, 2014; Bard and Faulkner, *Electrochemical*

Methods: Fundamentals and Applications; 2nd Edition, Wiley Press, New York, N.Y., 2001; Zhang et al. *Anal. Chem.*, 49:4778, 2007). With these improvements, miniaturized DNA-/aptamer-based sensors, specifically for the detection of DNAs and diagnostic proteins attract substantial attention, but their implemention in miRNA detection is rare (Sassolas et al., *Chem. Rev.*, 108:109, 2008). This is in part due to the key limitation of small sensor surface area when facing low abundance analytes, in which signal amplification is needed.

Enzyme amplification is routinely used in bioassays for detection. This includes redox enzymes used in i.e. glucometer (electrical detection) and enzyme-linked immunosobent assay (ELISA) (optical detection). However, no redox enzymes or antibodies have been shown to directly recognize nucleic acids or to generate/amplify detection signals. To employ enzymes for detecting nucleic acids, additional steps are required that complicate the detection. Similar limitations apply to various nanomaterials detection strategies being developed (Dong et al., *Chem. Rev.*, 113:6207, 2013; Sassolas et al., *Chem. Rev.*, 108:109, 2008).

SUMMARY

This invention is based, in part, on our discovery of an essentially one-step, label-free system comprising a sensing unit having a redox current reporter and a nucleic acid sequence complementary to that of a target nucleic acid of interest (i.e., 100% of the nucleic acid sequence of the sensing unit can be complementary to a sequence found in the target nucleic acid) or sufficiently complementary to that of the target nucleic acid or a sequence therein to specifically bind the target nucleic acid (i.e., less than 100% of the nucleic acid sequence of the sensing unit can be complementary to a sequence found in the target nucleic acid). Regarding complementarity, the nucleic acid sequence within the sensing unit that is complementary to the nucleic acid sequence of a target can be at least 80%, 85%, 90%, 95%, or 97% identical to the target sequence provided the two sequences anneal to the exclusion of non-target sequences under the conditions in which the system is used.

The sensing unit is bound to an electroconductive substrate (e.g., a carbon- or metal-containing microelectrode (e.g., a gold microelectrode)), and the system includes a signal amplification mechanism that does not rely upon a redox enzyme and thereby overcomes a fundamental limitation of microelectrode DNA sensors that fail to generate detectable current in the presence of only small amounts of a target nucleic acid. By employing a reductant in the buffer solution bathing the sensing units, the redox current reporters are cyclically oxidized at the electrode and reduced by the reductant, thus the signal is amplified in situ during the detection period. For example, the reductant can be, but is not limited to, tris-(2-carboxyethyl) phosphine hydrochloride (TCEP) or ascorbic acid (vitamin). By "reductant" we mean a reagent that will reduce the oxidized redox current reporter under the conditions in which the present sensors are used. Alternatively, the redox current reporters can be selected to be cyclically reduced by the electrode substrate and oxidized by the oxidant (instead of the reductant) in the buffer solution, thus the signal is amplified in situ during the detection. By "oxidant" we mean a reagent that will oxidize the reduced redox current reporter under the conditions in which the present sensors are used. Singly or collectively, we may refer to a reductant or an oxidant as a co-reactant.

The system can include multiple detection modes based on cyclic voltammetry and pulse voltammetry techniques (such as square wave voltammetry and differential pulse voltammetry). The parallel detection modes/methods combine the high sensitivity of pulse voltammetry for detection and the previously inaccessible diagnostic power of cyclic voltammetry for method validation and optimization. Previously, cyclic voltammetry techniques could not be used due to the low signals, while pulse voltammetry signals from an unknown sample could highly depend on the measurement parameters and generate false positive or false negative responses. As described further below, we were able to obtain a detection limit of a nucleic acid (an miRNA) as low as 0.1 femtomolar (fM) via direct readout, with a wide detection range from sub-femtomolar (fM) to nanomolar (nM) amounts. We were also able to detect sub-attomole miR-122 molecules. Moreover, detection occurs within minutes, which is a significant improvement over macroscopic sensors and other detection techniques such as qRT-PCR.

Accordingly, in a first aspect, the invention features systems for detecting a target nucleic acid in a sample. The systems include an electroconductive substrate; a sensing unit that is bound to the substrate; and a solution comprising a co-reactant and common buffer (e.g., a phosphate buffer). The composition of the solution can vary provided it permits the co-reactant to donate or receive electrons from the redox current reporter and permits hybridization between the nucleic acid sequences in the sensing unit and the sample being tested. The systems can be configured in any of the embodiments described herein to have a detection level as described above and elsewhere herein. The sensing unit includes a redox current reporter or a functional variant thereof. By "functional variant" we mean a molecule that varies from the current reporter referenced (e.g., methylene blue or a functional variant thereof) but retains the ability to function in the present system by donating electrons to or receiving electrons from the redox current reporter. The redox current reporter can be, for example, methylene blue, ferrocene or a derivative thereof, $Co(bpy)_3^{3+}$, $Co(phen)_3^{3+}$, daunomycin, Hoechst 33258, or other molecules and complexes that will undergo oxidation or reduction electron transfer reactions with the electrode at a given potential). The sensing units also include a nucleic acid sequence complementary to that of the target nucleic acid (e.g., a microRNA (miRNA) or a precursor thereof). For example, the nucleic acid sequence can be about 12-32 nucleotides in length (e.g., about 17-27 nucleotides in length (e.g., about 12, 13, 14, 15, 16, 17, 18, 19, 20, 21, 22, 23, 24, 25, 26, 27, 28, 29, 30, 31, or 32 nucleotides in length)). By "about" we mean a value rounded appropriately by plus-or-minus 10%. For example, a nucleic acid sequence that is about 20 nucleotides long, can be 18-22 nucleotides long. Suitable target nucleic acids include genomic DNA, cellular DNA, acellular DNA, microorganismal DNA, messenger RNA (mRNA), transfer RNA (tRNA), ribosomal RNA (rRNA), viral RNA, and a small nuclear RNA (snRNA). Moreover, the target nucleic acid can be obtained from virtually any source, whether animate or inanimate (e.g., inanimate objects such as fabrics, weapons, and personal care items can be tested for the presence and/or amount of a target nucleic acid sequence). The electroconductive substrate can include a carbon- or metal-containing microelectrode and can be variously fashioned (e.g., as a microelectrode having a radius or dimension of about 0.1-100 μm, a nanoelectrode having a radius or dimension below about 0.1 micron, or a macroelectrode having a radius or dimension above about 100 microns).

The sensing unit can be bound to the substrate through a variety of moieties, including thiolate moieties.

The systems described herein can further include alkanethiolate moieties (e.g., alkanethiol moieties) bound to the substrate to passivate the system and thereby reduce non-specific signals. More generally, any of the systems described herein can include passivating moieties.

In the systems of the invention, the co-reactant can be a reductant such as oxalic acid ($C_2H_2O_4$), formic acid (HCOOH), ascorbic acid ($C_6H_8O_8$), a compound comprising an $Sn^{2+}$ ion or $Fe^{2+}$ ion, hydrazine, tris-(2-carboxyethyl) phosphine hydrochloride (TCEP), or any other reagent that will reduce an oxidized redox current reporter. Alternatively, in the systems of the invention, the co-reactant can be an oxidant such as oxygen, hydrogen peroxide or other reactive oxygen species, a compound comprising an $Fe^{3+}$ ion, a compound comprising $ClO_4^-$, $BO_3^-$, $MnO_4^-$, $SO_5^{2-}$, $S_2O_8^{2-}$, $HSO_5^-$, $ClO_2^-$ or other halogen-containing anions, or any other reagent that will oxidize a reduced redox current reporter. If desired, more than one type of reductant or more than one type of oxidant can be included.

The systems of the invention can include sensing units that lack a redox enzyme.

The systems of the invention can be configured for high throughput screening of a plurality of nucleic acids. For example, the systems can include a plurality of sensing units, with a first sensor designed to detect a first nucleic acid and a second sensor designed to detect a second nucleic acid, wherein levels of expression of the first and second nucleic acids together signify the presence of a disease state. To detect additional nucleic acids, the systems can include additional target-specific sensors (e.g., 3-12 sensors).

In another aspect, the invention features methods of detecting a target nucleic acid in a sample. The methods can include the steps of: providing a sample that includes nucleic acids obtained from, for example, a subject or from a patient; and exposing the sample to a system as described herein. The subject can be a human or other mammal, and the sample can include blood, plasma, serum, sputum or saliva, cerebrospinal fluid, or urine. The sample can also be a tissue sample and can include tissue obtained in the course of a biopsy or other medical procedure. In one embodiment, the methods can be carried out to detect miR-122. In other embodiments, the system can include a plurality of sensing units configured to quantify the concentration of the microRNAs in a plurality of microRNAs associated with a disease state or condition (e.g., cancer, a neurological disease (e.g., a neurodegenerative disease), a cardiovascular disease, a metabolic disease or condition (e.g., metabolic syndrome or diabetes), an inflammatory condition, an infection, or an autoimmune disease). For example, the cancer can be hepatocellular cancer and the miRNA can be miR-122. In the event of a suspected infection, the sample can be obtained from a human and the system can be configured to detect a target nucleic acid from a pathogen (e.g., a bacterial, fungal, or viral pathogen).

In another aspect, the invention features methods of making a system as described herein. The methods can include the steps of (a) providing an electroconductive substrate; (b) immersing the substrate in a solution comprising sensing units for a time sufficient to allow the sensing units to self-assemble on the surface of the substrate, thereby generating a probe-functionalized substrate; and, optionally, (c) immersing the probe-functionalized substrate in a solution comprising passivating agents for a time sufficient to allow the agents to self-assemble on the surface of the substrate. For example, the sensing unit can include a sulfhydryl group, alkyne, or any functional group that provides precursors to bind to the electroconductive substrate.

The passivating agents can include sulfhydryl group. For example, the passivating agent can be an alkanethiol. In some embodiments, the methods can further include a step of immersing the probe-functionalized substrate in a solution comprising inert thiol moieties and heating and cooling the solution.

Systems that allow for better detection of nucleic acids, including circulating miRNAs that serve as disease biomarkers, should advance our ability to diagnose and treat disease. Such systems should also enable biomedical researchers to establish new miRNA patterns as biomarkers for different diseases and disease progression, including those configured to detect quite complex expression patterns. Currently available systems are not ideal and are challenged by the low concentrations and wide dynamic range (from aM (attomolar) to nM (nanomolar)) of miRNAs in physiological samples as well as high cost. Other features and advantages of the invention may be apparent from the following description, the drawings, and the claims.

BRIEF DESCRIPTION OF THE DRAWINGS

FIGS. 3A and 3B are voltammograms obtained with an miRNA sensing unit in TCEP and hybridization buffer at pH 7.1. FIG. 3A is a cyclic voltammogram (CV) recorded at a scan rate of 5 V $s^{-1}$. Clean background was obtained in buffer only (blue). The absence of the current from redox molecules indicates almost ideal sensor surface in the absence of target miRNA after a two-step passivation procedure. The good sensor surface coverage is also attested from the successful suppression of $O_2$ reduction. Addition of 160 μM TCEP or 0.5 nM miR-122 in hybridization buffer results in an increase of charging current with irresolvable or barely resolvable anodic current (black or green). Addition of both TCEP and miR-122 exhibits greatly improved oxidative current signal (red). FIG. 3B is a corresponding anodic square wave voltammogram (SWV) of the sensing unit. Data were recorded at a frequency of 100 Hz.

FIGS. 4A and 4B are voltammograms illustrating differentiation of the faradic ET current (current generated from electron transfer (ET) reactions) induced by target nucleic acid-binding from the capacitive background current. Data were recorded in 0.5 nM miR-122 and in the presence of 160 μM TCEP. FIG. 4A is a CV at different scan rates. The inset shows a linear correlation between the anodic peak current and scan rate. FIG. 4B is a SWV at different frequencies (scan rates). Baseline was adjusted to better display the trend.

FIG. 5A is a CV and FIG. 5B is a SWV at representative concentrations. CV data were recorded at a scan rate of 5 V $s^{-1}$ at 10 minutes after the addition of the target nucleic acid. SWV frequency is 100 Hz. The sensor was regenerated (overlapping black curves in (B) as background demonstrating the excellent sensor recovery) following each measurement by simple wash with 4 M guanidine chloride (GHCl). FIG. 5C illustrates the quantitative correlation between the integrated signal in SWV and miR-122 concentration over a wide range from 0.1 fM to 0.5 nM. The inset shows the trend at the lower concentration range in log plot. All data represent the average and standard deviation of two sensors. The error bars on some points are too small to be seen. The dashed line was added to illustrate the trend (not fitting).

FIG. 8A is a graph including a series of voltammograms that show the increase of detection signal over time. The kinetic responses of the sensor were recorded by square wave voltammetry (SWV) in the detection of 100 fM miR-122 at 1K Hz. SWV was recorded every 3 min from 0 to 30 min after target addition then every 5 min till 60 min. FIG. 8B is a plot graph of the detected peak current (along the arrow in FIG. 8) over time. FIG. 8C is a plot graph of current increase rate over different concentrations of the detected miR-122. The current increase rate at each of the concentration was respectively calculated based on a peak current-time plot in the initial 30 min of the incubation period (e.g., the plot over the first 30 min in FIGS. 8A and/or 8B) at the concentration.

DETAILED DESCRIPTION

Figure 1:
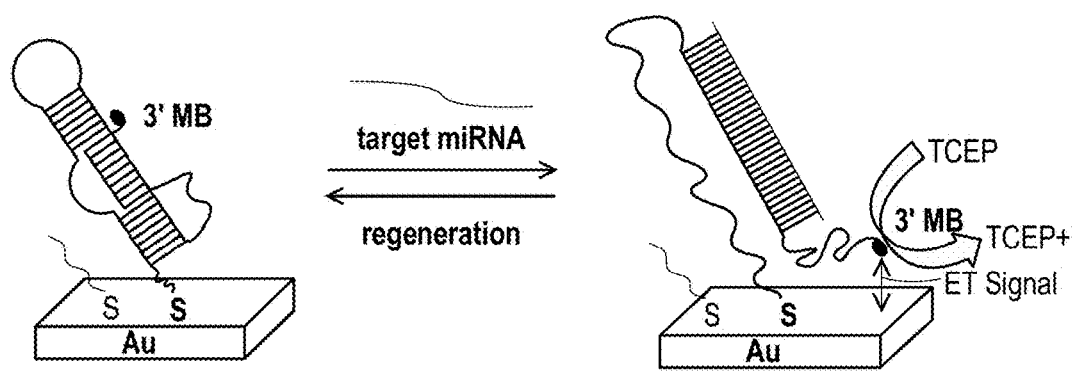
FIG. 1 illustrates a system for signal (current) amplification when a sensing unit binds a target miRNA as described herein.

A system as described herein is illustrated in FIG. 1. As indicated, an example of the sensing unit includes a sequence-specific nucleic acid, which is designed to hybridize with a target nucleic acid, such as an miRNA. The sensing unit also includes a redox current reporter, such as a methylene blue (MB) moiety, linked to the sequence-specific nucleic acid. When a sample containing target miRNA is added to the system, the target miRNA binds the complementary sequence in the sensing unit, and the redox current reporter is freed to move closer to the electroconductive substrate, where it is cyclically oxidized by the electrode, and then chemically reduced by the reductant (here, TCEP). Inert moieties, illustrated in FIG. 1 by OH-terminated C6 thiols, are also covalently bound to the surface of the electroconductive substrate (here, Au), passivating the surface of the substrate and supporting the sensing units. Each sensing unit will include a redox current reporter. In addition to, or as an alternative to, methylene blue, this reporter can be ferrocene or a derivative thereof, Co(bpy)$_3^{3+}$, Co(phen)$_3^{3+}$, daunomycin, Hoechst 33258, or other complexes and molecules with appropriate redox activities (by appropriate we mean the redox current reporter can cyclically undergo ET reactions with electrode (without reacting with media) and react with the coreactant (TCEP in this example)). Each sensing unit will also include a nucleic acid sequence that selectively binds the target nucleic acid. The sequences of the nucleic acid within the binding portion of the sensing unit will be sufficiently complementary to the sequences of the target nucleic acid, so that the binding portion will selectively bind to the target nucleic acid. The nucleic acid in the sensing unit can be generated from DNA or RNA as well as artificial or modified nucleic acids such as peptide nucleic acids (PNAs) and locked nucleic acids (LNAs). The sensing unit can be manufactured and used as described in Xiao et al., (*J. Am. Chem. Soc.* 131(42):15311-15316, 2009) and/or in Seelig et al. (U.S. Patent Application Publication No. 2014/0302486), both of which are hereby incorporated by reference herein in their entirety.

Sensing Unit Electroconductive Substrates:

The electroconductive substrate can comprise a carbon- or metal-containing microelectrode (e.g., a gold microelectrode). The sensing unit can be bound to the substrate non-covalently, or covalently (e.g., through a thiolate moiety), and the substrate can further be bound to moieties that do not contain sensing units (e.g., alkanethiolate). These "small non-sensing" moieties passivate the unoccupied sites on the substrate and thereby reduce non-specific signals.

Solutions and Coreactants:

In use, the sensing unit is immersed in a solution comprising a coreactant, and optionally, a common buffer.

In certain embodiments, the redox current reporter can include a molecule capable of undergoing oxidation and transferring electrons to the substrate, and the coreactant can be a reductant. The reductant can be an agent that is capable of reducing the oxidized redox current reporter. For examples, the reductant can be oxalic acid ($C_2H_2O_4$), formic acid (HCOOH), ascorbic acid ($C_6H_8O_8$), tris-(2-carboxyethyl) phosphine hydrochloride (TCEP), or any other reagent that will reduce the oxidized redox current reporter. In alternative embodiments, the redox current reporter can include a molecule capable of undergoing reduction and transferring electrons from the substrate, and the coreactant can be an oxidant that is capable of oxidizing the reduced redox current reporter.

Common buffers include but are not limited to phosphate buffered saline, TAPS (3-[[1,3-dihydroxy-2-(hydroxymethyl)propan-2-yl]amino]propane-1-sulfonic acid), bicine, tricine, TAPSO, HEPES, Tris, TES, MOPS, PIPES, cacodylate, SSC, MES, or succinic acid buffer.

Target Nucleic Acids:

Target nucleic acids can be microRNAs (miRNAs) or a precursor thereof, genomic DNA, cellular DNA, acellular DNA, microorganismal DNA, messenger RNA (mRNA), transfer RNA (tRNA), ribosomal RNA (rRNA), viral RNA, or a small nuclear RNA (snRNA). The present systems can be configured to detect the presence or absence of one or more single base mutations in a double-stranded target nucleic acid molecule and include a sensing unit that is designed to hybridize with the double-stranded and denatured target nucleic acid molecule in a reaction which proceeds at approximate thermodynamic equilibrium when no single base mutations are present in the double-stranded target nucleic acid molecule. The point mutations detected can be deletions, insertions, substitutions or single nucleotide polymorphisms (SNPs) in a target nucleic acid. Biologically significant or pathogenic processes may be indicated by a single base alteration or mutation within a target nucleic acid.

The target nucleic acids can be obtained from any biological sample. For example, the sample can be obtained from a human subject or other mammal such as a domesticated animal or livestock. The sample can also be obtained from cells (e.g., the cells of a cell line) or tissue maintained ex vivo in tissue culture or in a frozen or other preserved state. The sample may include, for example, blood, plasma, serum, bone marrow, cerebrospinal fluid, urine, or any diseased tissue (e.g., tissue obtained from a tumor biopsy, by lavage, or from a ductal system).

In certain embodiments, the present systems can be configured to detect, or quantify, a target nucleic acid that is present in a sample at, or below, a low level. The low level can be a millimolar level (e.g., 1, 2, 3, 4, 5, 6, 7, 8, or 9 mM), a micromolar level (e.g., 1, 2, 3, 4, 5, 6, 7, 8, or 9 µM), a nanomolar level (e.g., 1, 2, 3, 4, 5, 6, 7, 8, or 9 nM), a picomolar level (e.g., 1, 2, 3, 4, 5, 6, 7, 8, or 9 pM), a femtomolar level (e.g., 1, 2, 3, 4, 5, 6, 7, 8, or 9 fM), an attomolar level (e.g., 1, 2, 3, 4, 5, 6, 7, 8, or 9 aM), a zeptomolar level (e.g., 1, 2, 3, 4, 5, 6, 7, 8, or 9 zM), a yoctomolar level (e.g., 1, 2, 3, 4, 5, 6, 7, 8, or 9 yM), or a level therebetween.

In some embodiments, the present systems can be embedded in or otherwise part of a paper-based or polymer-based diagnostic tool, such as a lateral flow device or printed electrode arrays. A paper-based diagnostic tool can include a reaction with a visual readout, such as a paper-based microfluidic device or a lateral flow test based on the wicking of a sample through a matrix or other interface treated with biochemical reagents that are known in the art.

The present systems can be configured with a plurality of sensing units (a first sensing unit designed to detect a first target nucleic acid; a second sensing unit designed to detect a second target nucleic acid; and so forth) and can therefore by used in high throughput screening assays.

Quantitative Methods:

The present system can be configured to determine the level (e.g., concentration) of the target nucleic acid in a sample. The system can be used in connection with various suitable quantitative methods that are known for detecting or quantifying nucleic acids (e.g., Dong et al. *Chem. Rev.* 113:6207, 2013; Hunt, et al., *Annu. Rev. Anal. Chem.* 8:217, 2015).

In certain embodiments, the system can be calibrated with one or more standard solutions, and each of the standard solutions can contain a known concentration of the target nucleic acid. By measuring the signals of the system (e.g., the generated current) in the standard solutions, a quantitative correlation between the signal and the concentration of the target nucleic acid can be generated. The quantitative correlation can be used to determine the level of the target nucleic acid in the sample from the measured signal of the system in the sample.

Measurement of Signals:

During the detection or quantification of the target nucleic acid, the signal (e.g., current) generated by the present system can be measured or analyzed by various suitable techniques. The signal can be measured by amperometry, chronoamperometry, differential pulse voltammetry, cyclic voltammetry, square wave voltammetry, or any combination thereof.

Diagnostic Methods:

A system as described herein can include a first sensor designed to detect a first nucleic acid and a second sensor designed to detect a second nucleic acid, wherein levels of expression of the first and second nucleic acids together signify the presence of a disease state. For descriptions of cell-free miRNAs and a description of serum miRNAs as biomarkers for cancer diagnosis, see Brase et al. *Molecular Cancer* 9:306, 2010, Zen (Zen et al., *Med. Res. Rev.* 32(2): 326-348, 2012, and Zhang (Zhang et al., *World J. Gastroenterol.* 21(34):9853-9862, 2015).

More specifically, the systems described herein can include sensing units configured to detect miRNA-155, miRNA-210, and miRNA-21, and such systems are useful in diagnosing diffuse large B cell lymphoma, as the expression levels of miRNA-155, -210, and -21 are higher in the sera of patients who have developed diffuse large B cell lymphoma (Lawrie et al., *Br. J. Haematol* 141:672, 2008). High serum levels of miRNA-21 are also associated with relapse-free survival (Dong et al., *Chemical Reviews* 113:6207, 2013). Accordingly, the present methods can be used to determine the prognosis for a patient with diffuse large B cell lymphoma, with persistently high levels of miRNA-21 (but not miRNA-155 or miRNA-210) indicating an increased likelihood of relapse-free survival. When a sensing unit is "configured to detect" a targeted nucleic acid (i.e., a nucleic acid of interest), the sensing unit will contain a nucleic acid sequence that is the reverse and complement of the target or a portion thereof, and specific binding between the targeted nucleic acid and the nucleic acid in the sensing unit allows the targeted nucleic acid to be selectively bound and thereby detected.

In another embodiment, the systems include sensing units configured to detect let-7a, miRNA-155 and miRNA-195 in diagnosing breast cancer, and/or to distinguish the breast cancer from benign disease (Heneghan et al., *Ann. Surg.* 251:499, 2010; Zhu et al., *BMC Res. Notes* 2:89, 2009).

In another embodiment, the systems include sensing units configured to detect miRNA-29, miRNA-92a, miR-17-3p and miR-92 in diagnosing colon cancer, and/or to distinguish the colon cancer from benign disease (Huang et al., *Int. J. Cancer* 127:118, 2010; Ng et al., *Gut.* 58:1375, 2009).

In another embodiment, the systems include sensing units configured to detect miR-17-5p, miR-21, miR-106a, miR-106b and let-7a in diagnosing gastric cancer, and/or to distinguish the gastric cancer from benign disease (Tsujiura et al., *Br. J. Cancer* 102:1174, 2010).

In another embodiment, the systems include sensing units configured to detect miRNA-92a in diagnosing leukemia, and/or to distinguish the leukemia from benign disease (Tanaka et al., *PLOS ONE* 4:e5523, 2009).

In another embodiment, the systems include sensing units configured to detect miRNA-25, miRNA-223, miR-486, miR-30d, miR-1 and miR-499 in diagnosing lung cancer, and/or to distinguish the lung cancer from benign disease (Chen et al., *Cell Res.* 18:997, 2008; Hu et al., *Clin. Oncol.* 28:1721, 2010).

In another embodiment, the systems include sensing units configured to detect miR-31 in diagnosing oral cancer, and/or to distinguish the oral cancer from benign disease (Liu et al., *Oral Dis.* 16:360, 2010).

In another embodiment, the systems include sensing units configured to detect miRNA-21, miRNA-92, miRNA-93, miRNA-126, miRNA-29a, miRNA-155, miRNA-127, miRNA-99b in diagnosing ovarian cancer, and/or to distinguish the ovarian cancer from benign disease (Resnik et al. *Gynecol. Oncol.* 112:55, 2009).

In another embodiment, the systems include sensing units configured to detect miRNA-210, miR-21, miR-155, miR-196a in diagnosing pancreatic cancer, and/or to distinguish the pancreatic cancer from benign disease (Ho et al., *Transl. Oncol.* 3:109, 2010; Wang et al., *Cancer Prev. Res.* (Phila. Pa.) 2:807, 2009).

In another embodiment, the systems include sensing units configured to detect miRNA-141, miRNA-375 in diagnosing prostate cancer, and/or to distinguish the prostate cancer from benign disease (Mitchell et al., *Proc. Natl. Acad. Sci. USA* 105:10513, 2008; Brase et al., *Int. J. Cancer* 128:608, 2011).

In another embodiment, the systems include sensing units configured to detect miRNA-184 in diagnosing squamous cell carcinoma, and/or to distinguish the squamous cell carcinoma from benign disease (Wong et al., *Clin. Cancer Res.* 14:2588, 2008).

In another aspect, the invention features methods of making the systems described herein, and the assembled systems or component parts thereof can be packaged as a kit together with instructions for use.

EXAMPLES

The invention will be further illustrated in the following non-limiting examples. The following methods and techniques were used in the studies described below.

Reagents and Materials:

All solutions were prepared with RNase/DNase-free, ultrapure distilled water (Invitrogen). The following reagents were used as received: phosphate buffered saline (PBS; pH 7.4; 10×; Life Technologies), magnesium chloride hexahydrate (99-102%; Sigma-Aldrich), guanidine hydrochloride (≥99%; Sigma-Aldrich), tris-(2-carboxyethyl) phosphine hydrochloride (TCEP; ≥98%; Sigma-Aldrich), and 6-mercapto-1-hexanol (97%; Sigma-Aldrich). Thiolated, methylene blue-conjugated DNA (thio-MB-DNA) and micro RNAs (miR) were purchased from Biosearch Technologies (Novato, Calif.) and purified by RP-HPLC. The sequences of DNA probes and single-stranded miRNAs used in this work are given in Table 1.

Preparation of the Electrode and DNA Monolayer Assembly: Gold microelectrode fabrication was carried out using a well-established method. Briefly, a 50 μm-diameter gold wire was attached to a tugsten rod using conductive silver epoxy. The gold-tungsten assembly was then inserted into a soda lime glass capillary and then the gold wire was sealed into the capillary using a natural gas-oxygen flame. The other end of the assembly was secured with a resin epoxy. Finally, the excess insulating glass is removed through manual polishing on sand paper (from rough to find grit) to expose a gold wire resulting in a microdisk electrode with a 50 μm diameter. The gold electrode was polished carefully to a mirror surface on a 1200-grit sand paper followed by an aqueous slurry of 0.05 μm diameter alumina particles and then successively washed in an ultrasonic cleaner with water to remove excess polishing particles. Finally, the gold electrode was electrochemically polished by scanning the potential from −0.5 to +1.5 V in 0.1 M H2SO4 at a scan rate of 0.1 V s-1 for 10 cycles. The cleaned gold electrode was thoroughly washed with D.I. water and ethanol and dried under flowing nitrogen.

Prior to surface modification, 1 μL of 200 μM thio-MB-DNA was mixed with 2 μL of 25 mM TCEP in a 200-4, PCR tube. The tube was incubated for 20 minutes at room temperature (21° C.) for reduction of disulfide bonds and to reduce the MB-moiety of the DNA probe. The solution was then diluted to a total volume of 200 μL in a high salt buffer (10 mM potassium phosphate, 30 mM sodium phosphate, 1.55 M sodium chloride and 1 mM magnesium chloride, pH 7.2) to a final concentration of 1 μM. For immobilization, the previously cleaned gold electrode was transferred directly to the diluted and reduced thio-MB-DNA solution and incubated for 16 h at room temperature in the dark. Following the formation of a self-assembled monolayer (SAM), excess thio-MB-DNA physically adsorbed on the electrode surface was removed via a room temperature-deionized water rinse (~30 s). The surface was then passivated by immersing the electrode into a 1 mM mercaptohexanol in high salt buffer for 2 h. For optimal surface modification, the sensor was placed in a hybridization buffer (0.25 mM potassium phosphate, 0.75 mM sodium phosphate, 39 mM sodium chloride and 10 mM magnesium chloride, pH 7.1) and heated indirectly via a water bath of 75° C. for 10 min. After the surface cooled down, another passivation with 1 mM mercaptohexanol was performed for 1 h. Unless otherwise noted, all solutions used in the studies described below were carried out in hybridization buffer at pH 7.1. For convenient surface regeneration, hybridized sensors were rinsed in 4 M GHCl for 30 s followed by a 3-hour incubation in hybridization buffer.

Electrochemical Measurements:

Electrochemical measurements were performed using a Gamry Reference 600 electrochemistry workstation (Gamry Instruments, Warminster, Pa.) with a Ag/AgCl(s)/KCl(sat) reference electrode (Bioanalytical Systems, Inc.) and a gold working electrode. All potentials are reported relative to the saturated Ag/AgCl reference electrode. Electrochemical measurements were performed in hybridization buffer using cyclic voltammetry (CV) from −0.6 V to +0.2 V, or square wave voltammetry (SWV) with a 50 mV amplitude signal, over the range from −0.6 V to +0.1 V versus Ag/AgCl reference. The oxidative peak of MB was detected by CV or SWV at −200 mV (vs Ag/AgCl) at the 10-minute time point. MB was chosen as the redox tag due to its excellent shelf life and robust electrochemical response in serum compared to other redox tags, such as ferrocene (Kang et al., *J. Anal. Chem.* 81:9109, 2009). The SWV response of each sensor was quantified as follows: (1) background (without target) and signal (with target) SWV data sets were collected; (2) difference traces were generated by subtraction of the two data sets; (3) baseline was corrected with B-spline generated baseline in Origin 8 using two regions: −0.60 to −0.40 V and −0.08 to +0.10 V; (4) traces were integrated from −0.40 to −0.08 V. To prepare calibration graphs, we report the average and deviations of two measurements on two different sensors for relatively high miR-122 concentrations from 10 fM to 0.5 nM, while for the low miR-122 concentrations of 0.1 fM and 1 fM the average of three measurements on two different sensors is reported. Selectivity tests with mismatched sequences were made in the same manner by substituting miR-122-3p or miR 22B for miR-122. Prior to the measurement of colitis mouse serum, a serum aliquot of 2 was heated for 15 minutes at 95° C., followed by centrifuging to collect sample. Then, the serum aliquot was diluted in a 20 μL buffer solution for easy handling and to make the current signal comparable with calibration measurements at the time for detection. The sensor was incubated for 10 minutes at room temperature prior to data collection.

Study Overview:

The work below demonstrates a system having high selectivity and discrimination between two similar family sequences: miR-122-3p, present in serum, and a synthetic RNA sequence mismatched by two nucleotides. Interference, such as the nonspecific adsorption that is a common concern in sensor development, is reduced to negligible levels by adopting a multi-step surface modification strategy. Importantly, unlike qRT-PCR, the microelectrochemical sensor offers a direct absolute quantitative readout that is amenable to clinical and in-home or point-of-care applications. The sensor design is flexible, as it can be tailored to detect different nucleic acids (e.g., miRNAs) of interest, and the system can be configured for high throughput detection of nucleic acids (e.g., miRNAs), including those serving as disease biomarkers.

miRNA-122 has a unique sequence and is expressed in liver and conserved in vertebrates (Zhang et al., *Clin. Chem.*, 56:1830, 2010). Down-regulation is linked to hepatocellular carcinoma (HCC) and up-regulation is related to gastrointestinal disorders (Starkey Lewis et al., *Hepatology*, 54:1767, 2011; Coulouarn et al., *Oncogene* 28:3526, 2009). A self-hybridized, three-stem loop structure DNA sequence is designed following previous report by Plaxco and coworkers as a recognition probe (Xiao et al., *J. Am. Chem. Soc.*, 131:15311, 2009). The sensing unit includes a sequence that is complementary to that of the target miR-122 and methylene blue (MB) as a redox current reporter. To boost the low current associated with a small effective sensor surface, we introduce a chemical reaction mechanism following electron transfer reaction (Flynn et al., *Langmuir*, 19:10909, 2003) using the reductant TCEP (tris-(2-carboxyethyl) phosphine hydrochloride) in the solution surrounding the sensing units that reduces the oxidized MB in situ (Labib et al., *Anal. Chem.*, 87:1395, 2015). When the sequence-specific portion of the sensing unit recognizes its target nucleic acid in a sample, the redox current reporter (MB in this example) is freed to move nearer the electroconductive substrate, where it is cyclically oxidized electrochemically and reduced chemically by the reductant. This process amplifies the signal (Furst et al., *Polyhedron*, 84:150, 2014; Lapierre-Devlin et al., *Nano Lett.*, 5:1051, 2005; Fang and Kelley, *Anal. Chem.*, 81:612, 2009). Moreover, with our multi-step surface modification procedure, interference signals caused by non-specific adsorption and surface-bound redox current reporters are reduced to negligible levels. These interference signals are a well-known technical barrier for sensor development. Compared to other sensor-based detection methods, the signal amplification and background reduction we have achieved produce reproducible and reusable systems for rapid, quantitative, and easy (one-step) nucleic acid detection, even where the target nucleic acid is present at extremely low levels.

Figure 2A:
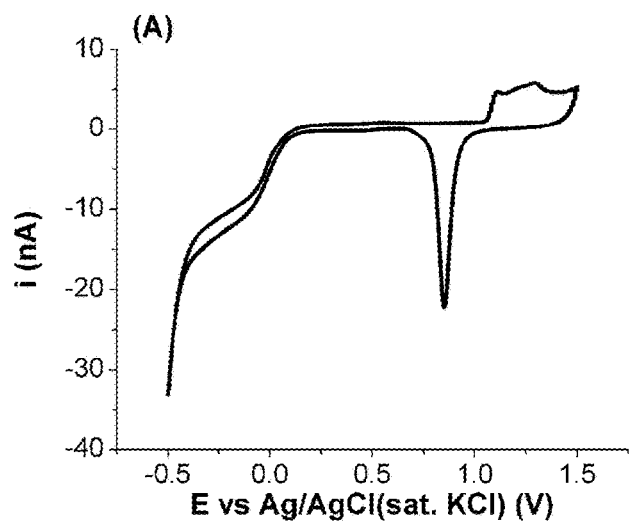
FIGS. 2A and 2B are traces characterizing a 25 μm (radius) gold microelectrode at 0.1 M $H_2SO_4$ at a scan rate of 100 mV $s^{-1}$ (A) and 1 mM ferrocene solution at a scan rate of 100 mV $s^{-1}$.
Figure 2B:
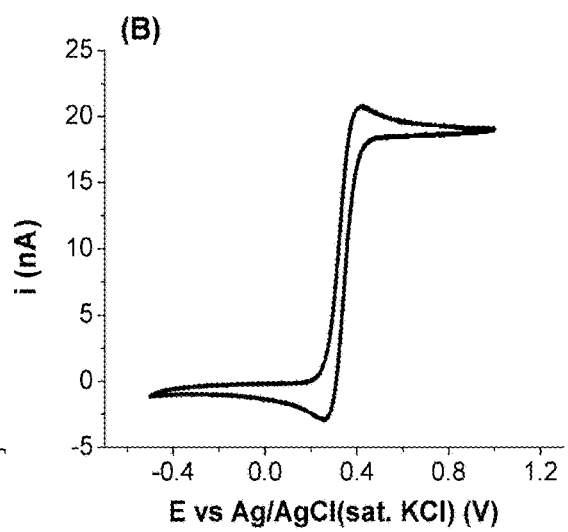

The principle of signal generation is illustrated in FIG. 1. The Au-disk microelectrode (radius r typically 25 µm) was prepared via a benchtop method that is routinely used in our lab for nanoelectrode fabrication and characterized with 1 mM ferrocene (FIGS. 2A and 2B; Liu et al., *Anal. Chem.*, 84:6926, 2012; Liu et al., *Langmuir*, 28:1588, 2012; Feng et al., *Anal. Chem.*, 82:4520, 2010). The signal-on mechanism upon the recognition with target miRNAs is designed following the electrochemical DNA sensor strategy described by Xiao et al. (*J. Am. Chem. Soc.*, 131:15311, 2009). The sensing unit is designed to have multiple nucleic acid segments, including a sequence perfectly complementary to the target nucleic acid (miRNA-122 in this study) and is bound to the electroconductive substrate by an alkanethiol moiety at the 5' terminus. This moiety allows for self-assembly onto gold surfaces. A MB moiety at the 3' terminus serves as the redox current reporter. The sequence of miR-122, a designed probe, and two mismatched sequences are shown in Table 1:

| Sequence Name | (Abbreviation) | Sequence, listed 5' to 3' |
|---|---|---|
| Triple-stem DNA probe | (DNA) | /C6 SS/ GGA GTG TTT TTT TTC GTG TTT GTT TTT TCA AAC ACC ATT GTC ACA CTC CAT TTT TTT TTG ACA ATG /MB/ (SEQ ID NO: 1) |
| mmu-miR-122 | (miR-122) | UGG AGU GUG ACA AUG GUG UUU G (SEQ ID NO: 2) |
| mmu-miR-122-3p | (miR-122-3p) | AGU GUG AUA AUG GCG UUU (SEQ ID NO: 3) |
| 2mismatch-22Base | (miR 22B) | UGG AGU GUG AUA AUG GCG UUU G (SEQ ID NO: 4) |

The triple-stem DNA probe (SEQ ID NO:1) is shown with the recognition sequence underlined. The target sequence is miR-122 (SEQ ID NO:2), and the mismatched sequences (miR-122-3p and miR 22B; SEQ ID NO:3 and SEQ ID NO:4, respectively) are shown with the mismatched nucleotides double underlined.

To design other sensing units to detect different miRNAs, the binding sequence (i.e., the sequence complementary to a target sequence) can be conveniently replaced. The base (as described further below) that sufficiently binds to the binding sequence can also be adjusted accordingly, so that in the absence of the target miRNA, the probe will self-hybridize into three distinct, short-base-pair stems that form a discontinuous double helix (see the left-hand side of FIG. 1). Once a new miRNA is selected as a target, a DNA sequence that selectively binds to the target miRNA will be established as the binding sequence in the overall sensing unit. Accordingly, multiple (e.g., three) separate short DNA segments will be synthesized so that the combination of those segments have the exact sequence of the target miRNA (or a sequence that sufficiently binds to the binding sequence in the absence of the target miRNA). Those short DNA sequences will form the base, and the binding sequence will be linked by an adjustable number of non-complementary nucleotides (e.g., a poly-T sequence) to form the overall sensing unit with the three-stem loop shown. With inert alkanethiolates passivating the surface unoccupied by the sensing units, the discontinuous double helix will lock the redox current reporter, MB, away from the electroconductive substrate, thus largely shutting down electron transfer pathways. A signal, in the form of faradic ET current, is generated only upon recognition of the target miRNA. Hybridization between the sensing unit and the target nucleic acid is energetically favored by the formation of a longer double strand over the disruption of the discontinuous triple-stem structure. The process of hybridization liberates a flexible segment near the MB-labeled 3' terminus, which in turn enables electron transfer (ET) between the redox current reporter and the electroconductive substrate that generates the faradaic ET current that reflects the concentration or quantity of the accessible miRNAs (see the right-hand side of FIG. 1).

We have developed a multi-step surface modification strategy to optimize the sensor surface and minimize background ET current. Most of the current electrochemical sensors allow for nonspecific adsorption to the substrate, which is detrimental because it induces interference signals that limit quantification, particularly for target nucleic acids at low abundance. The MB oxidation peak at −200 mV indicates a non-ideal surface after the commonly adopted one-step modification. It is rather common to have non-ideal surface packing with defect sites ("pin holes") in self-assembled monolayers. The redox current reporters can then interact with the electrode for ET after the first passivation step, generating target-independent background current. To improve the quality of the passivating monolayer and supress background current, we applied a heating/cooling cycle that allows rearrangement of the thiolates on the surface of the electroconductive substrate. After a second passivation step with the same inert thiols, baseline-level non-faradic charging current, which indicates an almost ideal surface modification, was achieved in both cyclic voltammetry (CV) and square wave voltammetry (SWV) measurements (blue curves in FIGS. 3A and 3B). This observation indicates that the "pin holes" in the thiolate layer are further filled by the alkanethiolates after the second passivation step. The resulting, high quality surface functionalization makes the system highly resistant to common interferences such as nonspecific adsorptions and also inhibits oxygen molecule permeation and the collapse of the sensing units.

A major limitation associated with surface-based electrochemical sensors is that the signal intensity depends on the surface coverage of probes. Once a MB molecule is oxidized at a given potential, it loses ET activity to generate the detection signal until reactivated via reduction. To enhance the sensitivity, we introduce a chemical reagent (reductant) in bulk solution that reduces the oxidized MB in situ at the detection potential. As shown in FIGS. 3A and 3B, well-resolved anodic current can be observed only in the present of both TCEP and miR-122, in both CV and SWV measurements (red curves). Only anodic peak currents were studied in this work due to the presence of oxygen reduction peak that overlaps partially with that of MB at ca. −0.3 to −0.4 V. As controls, negligible anodic currents were detected in CV in the presence of TCEP but without miR-122, suggesting that TCEP will not interfere with measurements within the detection potential window of MB (black curves). A slight distortion in baseline at around −0.4 V is consistently observed after the addition of TCEP, particularly in SWV. The distorted baseline measured prior to the addition of target is used as background current and subtracted from the signal current in the quantitative analysis. The miRNA-122 itself, without TCEP, causes a slight increase in anodic current in both CV and SWV that is barely discernible from baseline current. This low signal level constitutes a common problem for miniaturized electrodes and sensors in general. The parallel current traces in CV arise from simple capacitive charging and discharging of double layer that does not interfere with the data analysis elaborated in the later sections. An important aspect of the signal amplification is the reductive property of TCEP. In the detection system, each MB molecule that comes near the surface of the electroconductive substrate (as a consequence of the sensing unit recognizing a target nucleic acid), will be cyclically oxidized at the electrode and reduced by the reductant, which greatly amplifies the signal during the detection period. By analogy, the surface-bound sensing units can be considered to function as the Gate (with each MB as a "tunnel") while the reductant in solution and the electrode function as the "source" and "drain" in electron tunneling or field-effect transistors, respectively. Much effort has been expended in developing electrocatalytic strategies for DNA sensors. To the best of our knowledge, direct detection of ET current in CV has not been reported in the folding-based DNA electrochemical sensing literature, especially with microelectrodes. Pulsed techniques such as SWV or differential pulse voltammetry (DPV) were necessary to resolve the ET signals, which involve complex kinetics and could generate false positive or false negative responses under different measurement conditions. Non-specific physical/mechanical interactions could cause the sensing unit to collapse or deform, causing electron transfer between the collapsed sensing unit and the surface of the electroconductive substrate, which induce false positive signals (Labib et al., *J. Am. Chem. Soc.*, 135:3027, 2013; Labib et al., *Anal. Chem.*, 85:9422, 2013; Labib et al., *Anal. Chem.*, 87:1395, 2015). False negatives have been reported at extremely high frequencies, especially in the case of a target-saturated surface (White and Plaxco, *Anal. Chem.*, 82:73, 2010). Data from both CV and SWV will better reveal signal generation mechanism and thus enable better method design and development. Besides the signal amplification mechanism, we discovered that detection current can reach a measurable level at each concentration within 10 minutes, which is substantially faster than in counterpart gold electrodes fabricated on a macro scale (Xiao et al., *J. Am. Chem. Soc.*, 131:15311, 2009).

The faradic ET current signal resulting from the target recognition can be quantified and differentiated from background current (e.g., capacitive charging-discharging) at the surface of the electroconductive substrate under optimized measurement conditions. The observed CV features at different scan rates are characteristic of electrodes at the transition size range between macroelectrodes and ultramicro/nanoelectrodes. At relatively low scan rates (1 V/s or lower), the anodic current in CVs (FIG. 2A) shows a plateau that is characteristic of diffusion limited microelectrode behavior. This diffusion process corresponds to the TCEP from bulk to the surface of the sensing unit because MB is immobilized on the microelectrode. At faster scan rates (5 and 10 V/s), the mass transport rate is no longer sufficient relative to ET kinetics, thus depletion near the surface of the electroconductive substrate causes the anodic current to decrease at higher overpotentials. Accordingly, the CV features transform from micro- to macroelectrode-like behaviors. The shape transitions of CVs at different scan rate correspond to the TECP diffusion behavior by considering each methylene blue tunneling the electron transfer as an individual nanoelectrode: the plateau current corresponds to the radial diffusion of TCEP, while faster ET kinetics at high scan rate induces depletion peak shape (i.e. t-½ decay). A linear correlation was established between anodic peak current and scan rate rather than square root of scan rate. The linear dependence reflects the radial diffusion at the microelectrode and should not be confused as adsorption on macroelectrodes. It is important to mention that the current signal is enabled through surface-bound MB on the electrode. Baseline adjusted SWVs at varied frequencies further affirm the analysis (FIG. 4B). Because capacitive charging current is largely subtracted in SWVs, the current peak is better resolved. The peak current displays a linear relationship with frequency within the range tested. At higher frequencies, the peak current decreases, which is consistent with earlier reports that SWV peak current could decrease at higher frequency ranges at the DNA sensors (White and Plaxco, *Anal. Chem.*, 82:73, 2010). The frequency of 100 Hz was used in later measurements considering the less distorted baseline and the uncertainty of charging current in varying solution conditions as well as possible impacts by different kinetic processes in signal generation at higher frequency.

Figure 5A:
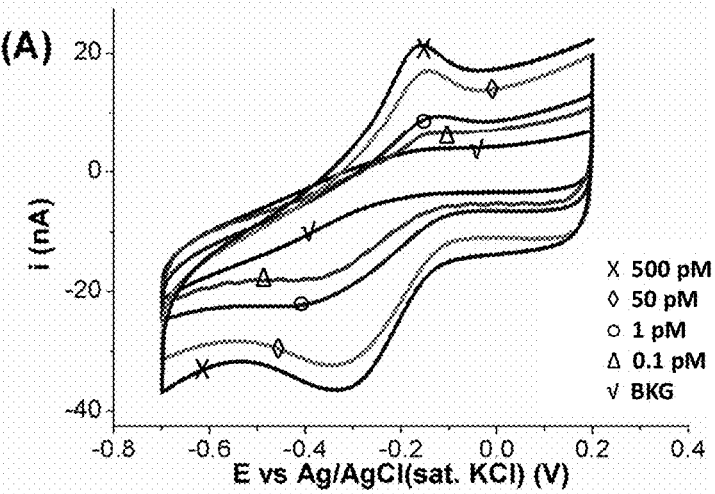
FIGS. 5A and 5B are voltammograms and FIG. 5C is a line graph illustrating sensor responses at different miR-122 concentrations.
Figure 5B:
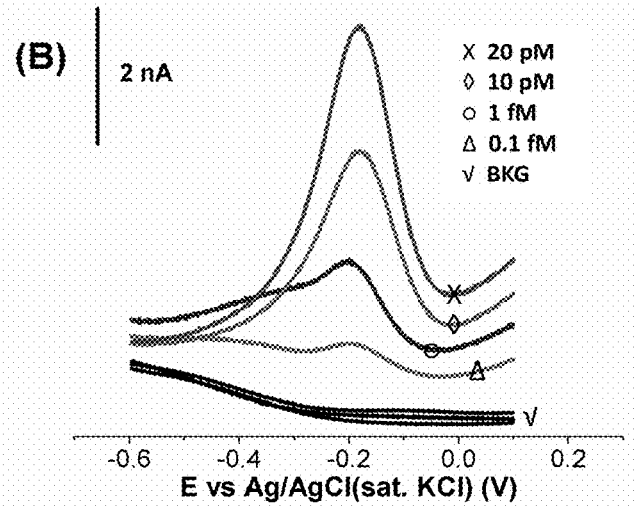

The microelectrode sensor was further challenged for the quantification of miR-122 in phosphate buffer solution at pH 7.1. As shown in FIG. 5A, baseline-level anodic current was attained in the presence of only TCEP in buffer solution for up to 160 µM as background (BKG). Upon each addition of miRNA-122 at the denoted concentration, the methylene blue peak current in CVs measured after a 10 minute incubation increased. The corresponding SWVs show a drastic improvement in resolving signals from background at miRNA-122 levels below 0.1 pM (FIG. 5B). However, it is known that the signal deliberated by SWV is highly dependent on the measurement parameters, such as frequency, due to its sensitive nature to electrode reaction rates (White and Plaxco, *Anal. Chem.*, 82:73, 2010).

The CVs, on the other hand, are better suited as diagnostic tool for method development. Previous studies could not take advantage of CVs because the current signal is generally too low to be detected. Both CV and SWVs were recorded at the mean time for parallel analysis and method validation. A large dynamic range (sub fM to nM) is established that could be further extended if necessary by the optimization in sensor design and measurement parameters.

Remarkably, the background current can be recovered repeatedly after each target miRNA measurement (bundled black curves in FIG. 5B). This demonstrates superb sensor stability and consistency, which are vital for quantification, method development, and optimization. A wide range of miR-122 concentrations (from 0.1 fM to 500 pM) were tested with two separate sensing units. Although variations due to the differences in surface area and probe coverage were observed, current signals resulting from the same miR-122 concentration on different sensors remained comparable. Impressively, a detection limit of 0.1 fM was achieved. This corresponds to 0.2 attomole of miR-122 molecules. A 20-microliter sample was sufficient, corresponding to the detection of 1200 copies miR-122 within 10 minutes. The capability of this system is approaching that of qRT-PCR but offers absolute quantification at drastically reduced time and cost.

Figure 5C:
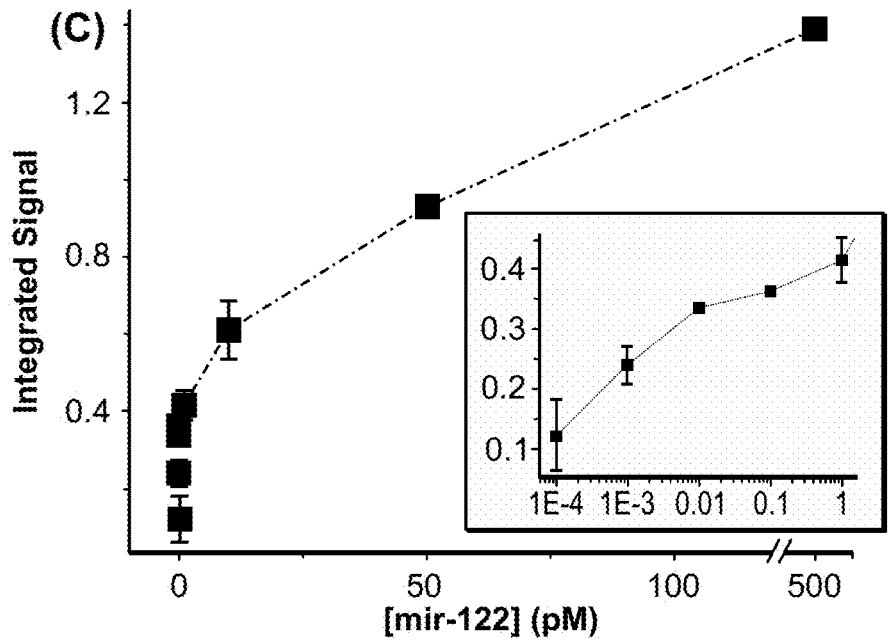
Figure 6:
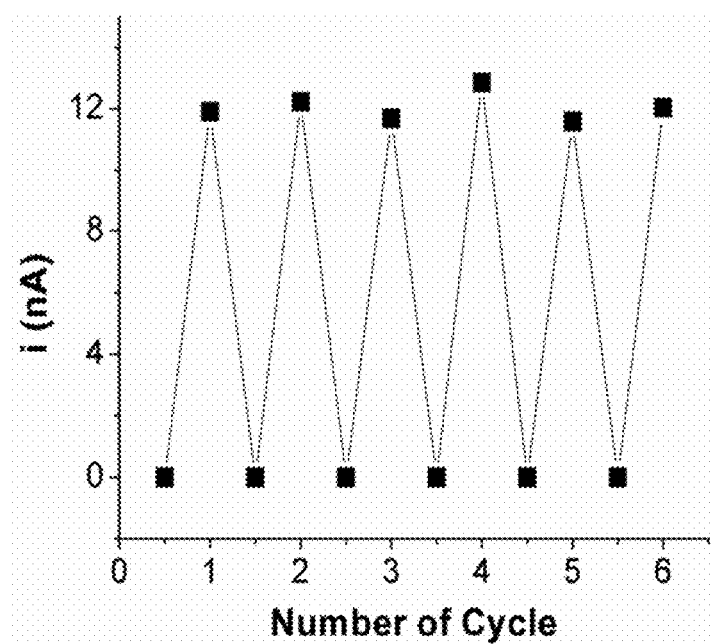
FIG. 6 is a line graph illustrating the regeneration and stability of the microelectrode-based electrochemical DNA-sensors. Reproducible results were achieved with GHCl wash in the detection of 50 pM miRNA-122. Sensors can be readily regenerated at least 6 times without any loss of sensitivity. Additionally, sensors can be stable after a 2-month storage in dry-form at room temperature. Current was obtained from CV measurements after charging current subtraction.

A langmuir isotherm-type curve was observed by plotting the integrated current signal from SWV as a function of miRNA-122 concentration as the calibration curve (FIG. 5C). Because the current peak shape is conserved, integrated peak area is proportional to peak current in the SWV results described herein. Analyzing integrated currents is superior to a single point analysis (peak current) as it allows ensemble averaging and reduces possible interference such as from random noise or baseline fluctuation. The trend is the direct consequence of the governing mechanism of signal generation. The detected current results from a series of kinetic processes including mass transport of miR-122 from solution to the surface, hybridization with surface DNA sequence, ET among the TCEP, MB and the electrode, and the diffusion of TCEP. For simplicity in establishing the signal amplification concept, the data in FIG. 5C were collected at a fixed time (10 minutes inculation). For a given surface area (i.e., 25 µm radius) over a given period (10 minutes), the sensor surface would be saturated at high concentrations (i.e. the last point in FIG. 5C) and thus the current signal approaches a plateau; while at low concentrations a qualitatively linear correlation with logarithm analyte concentration was detected as commonly observed for these types of sensors. In other words, a broad detection range over 6 orders of magnitude is established governed by different kinetic processes.

Figure 7:
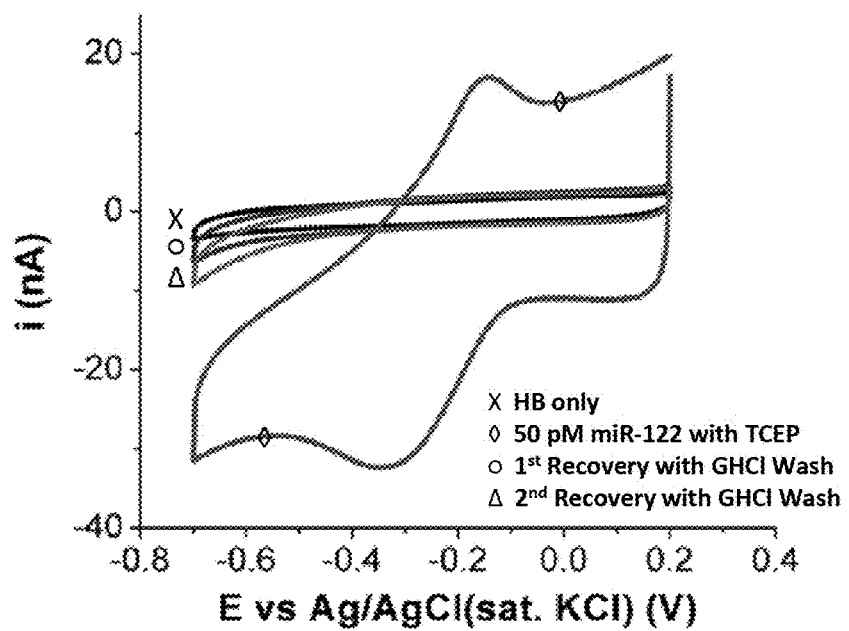
FIG. 7 is a line graph illustrating the stability of the sensing units. The sensing units can be regenerated by washing with 4 M GHCl for 30 seconds. The sensor response exhibited clean baseline hybridization buffer prior to each measurement and regenerable signal in the presence of miR-122. The recovery CVs (after regeneration) was recorded in hybridization buffer only at a scan rate of 5 V s$^{-1}$.

It is important for method validation and quantitative analysis that the sensing units can be conveniently regenerated, although it might not be critical for practical applications. The negligible, baseline-level background current can be regenerated after a 30-s room temperature wash with 4 M GHCl followed by a 3-h incubation in buffer solution repeatedly (FIG. 7). GHCl is known to disrupt hydrogen bonds in double stranded DNAs thus helping to release target miRNAs from surface-bonded DNA probes. Upon incubation in HB, the thermodynamically stable triple-stem structure is restored at room temperature within 3 hours. Accordingly, the sensing unit can be regenerated with a mean recovery of near 100% of the initial signal. A gradual rise of background current and decline of signal current become noticeable after more than six cycles for this sensing unit. The deterioration is attributed to the degradation of the thiolate SAMs (Flynn et al., *Langmuir*, 19:10909, 2003). If a resuable sensing unit is needed, the stability could be further improved by the optimization of the inert thiols, including using longer carbon chains for the inert spacer and employing multidentate thiols, for example (Srisombat et al., *Langmuir*, 24:7750, 2008). More excitingly, the sensing unit preserved its function after a two-month storage in dry form.

We evaluated the specificity of the sensing unit with two physiological analogs: a two-base mismatched miR-122-3p with 18 bases and a synthetic two-base mismatched miR 22B of 22 bases that has the same length as the target miR-122. Essentially no response was observed in the presence of 200 pM miR-122-3p or miR 22B even after a 30-minute incubation. To affirm the efficacy of this exact sensor, with a 10-fold lower miR-122 (20 pM), the signal raised substantially in 10 minutes. We believe the superior discrimination of mismatched bases at room temperature results from the distinct thermodynamic properties in the triple-stem structure regardless of the electrochemistry signal amplification mechanism. The location of the mismatches in the physiological analogs (i.e., in the middle of the sequences or toward the end), the identity of the mismatched bases as well as the length of the nonspecific sequences are factors to consider in the design of probes for other nucleic acids.

To illustrate the efficacy of the sensing unit in a complicated matrix and to mimic detection in real point-of-care settings, we tested a serum sample from a colitic mouse. The expected anodic current from the cyclical oxidation of MB and reduction by TCEP upon binding with target miRNAs was observed at 10 minutes in a diluted serum sample. The results suggest that the signal generation mechanism remains effective in the complex physiological matrix. A heating treatment of the serum sample seemed to be required because the miRNAs are either stabilized by proteins or encapsulated in vesicles in serum/blood. Therefore, the curve (without heating) illustrates the resistance of the sensor detection mechanism to the complicated matrix including nonspecific adsorption of proteins and lipids in physiological samples.

To demonstrate that common reductants other than TCEP could also be used, the sensor was tested using vitamin C in the detection of miR-122. Following the same procedure of TCEP analysis, similar sensor performance was obtained.

In summary, we used a common reductant, TCEP, and the target sequence miR-122 as a model system to demonstrate the sensor efficacy evaluated by potential sweeping CV and pulsed SWV techniques. As a benefit of the multi-step surface modification method, background current was minimized to the baseline level. Combining the pristine baseline (without target miR-122) and signal amplification by TCEP, we demonstrated the detection of miR-122 within minutes at an extremely low level with a wide detection range from 0.1 fM to 0.5 nM. The amplified current signal enabled one-step detection by CV at microelectrode sensors previously inaccessible. The combined diagnostic power in CV and the great sensitivity in SWV are highly advantageous in the present methods and in parameter optimization. Moreover, we could quantify the absolute miRNA abundance by direct electrochemical readouts, which is significant for biomedical research and bodes well for clinical and in-home or point-of-care applications. The sensing unit exhibited superior mismatch discrimination owing to the three-stem double helix design that has been validated in macroscopic electrochemical DNA sensors. The sensing unit preserves its function in diluted mouse serum for detection of miR-122 and exhibits outstanding resistance to interferences present in serum The excellent stability and reproducible surface regeneration with GHCl further enables systematic and quantitative analysis. The sensing unit design is generalizable for other nucleic acid sequences.

Figure 8A:
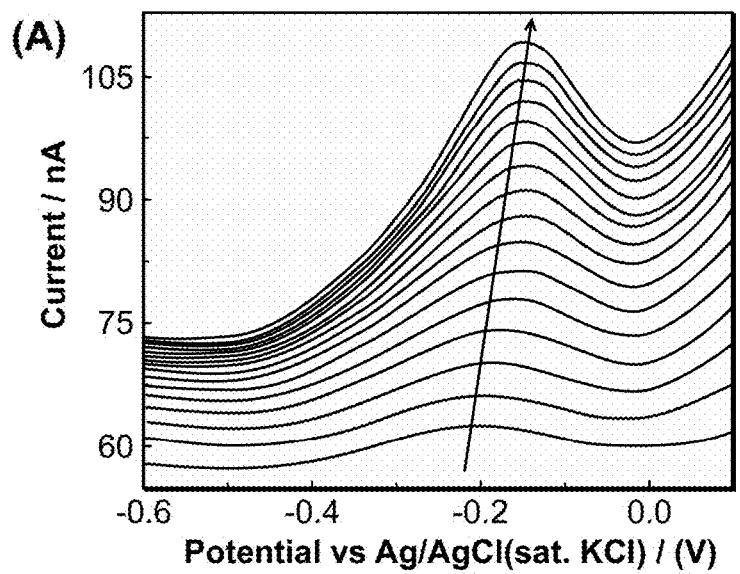
FIGS. 8A-C are graphs illustrating kinetics of the sensor performance.
Figure 8B:
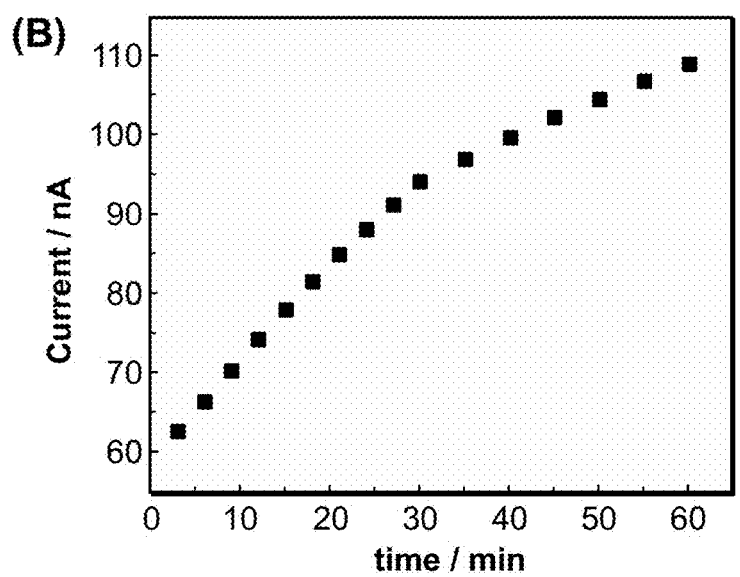
Figure 8C:
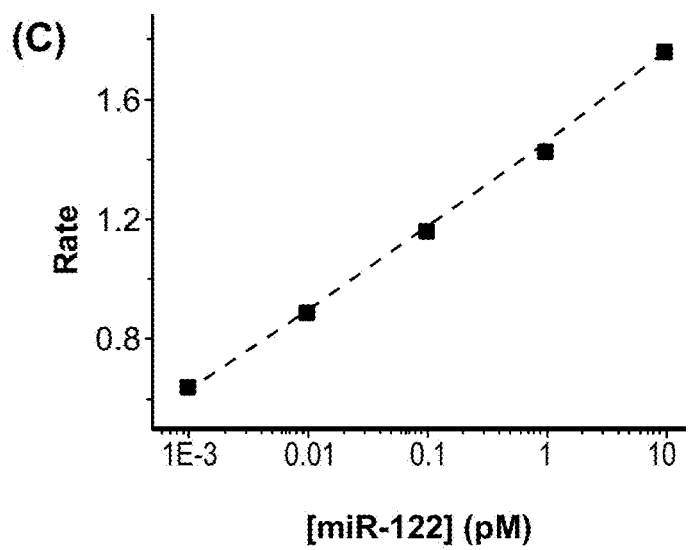

We further studied the kinetics of the sensor in detection of miR-122 (FIGS. 8A-C). As indicated by the arrow in FIG. 8A, the oxidation current of the methylene blue (MB) moiety in the sensor increases with the increased incubation time of the sensor in a solution of miR-122. As further illustrated in FIG. 8B, the rate of the current increase reduces over time, indicating the lessening of available sensing units as time increased. This observation suggests new routes to establish the sensor calibration profiles, underlines the significance to employ different methods for analyzing samples within different dynamic ranges based on the kinetics, and explains the fundamental reasons for the inefficacy of other sensors. In other words, this detection method can be established by a multi-point analysis-calibration, which is expected to be highly advantageous over a single point reading. In single-point measurement, one has to assume the sensor response for an unknown sample is in the same kinetics domain with the calibration profiles. A multi-point measurement, however, will increase signal-to-noise ratio by reducing random noise. A linear relationship was determined between rate of signal increase and the miR-122 concentration is shown in FIG. 8C as a proof of concept. Investigation is underway to establish better methods for signal quantitation to possibly further improve detection sensitivity and expand dynamic range.

Given that the sensing unit was developed on a small scale electrode, the established platform is promising as a high-throughput system, including for use in detecting miRNA signatures as disease biomarkers or, over a longer term, determining miRNA signatures to complement existing techniques such as qRT-PCR while offering direct quantification.

What is claimed is:

1. A system for detecting a target nucleic acid in a sample, the system comprising
   an electroconductive substrate;
   a sensing unit that is bound to the substrate, wherein the sensing unit comprises
      a redox current reporter and
      a sequence-specific nucleic acid,
         wherein the sequence-specific nucleic acid comprises a nucleic acid sequence that is sufficiently complementary to that of the target nucleic acid or a sequence therein to specifically bind the target nucleic acid,
         wherein the sequence-specific nucleic acid is a single nucleic acid strand, is bound to the substrate, and is not bound to the substrate via a separate nucleic acid strand,
         wherein the redox current reporter is linked to the sequence-specific nucleic acid; and
   a coreactant.

2. The system of claim 1, wherein the target nucleic acid is a microRNA (miRNA) or a precursor thereof.

3. The system of claim 1, wherein the electroconductive substrate comprises a carbon- or metal-containing microelectrode.

4. The system of claim 3, wherein the electroconductive substrate is fashioned as a microelectrode having a radius or dimension of about 0.1-100 μm, a nanoelectrode having a radius or dimension below 0.1 micron, or a macroelectrode having a radius or dimension above 100 micron.

5. The system of claim 1, wherein the sensing unit is covalently bound to the substrate.

6. The system of claim 1, wherein the sensing unit is bound to the substrate through a thiolate moiety.

7. The system of claim 1, further comprising alkanethiolate moieties bound to the substrate to passivate the system and thereby reduce non-specific signals.

8. The system of claim 1, wherein the redox current reporter comprises a molecule capable of undergoing oxidation, thereby transferring electrons to the substrate and generating an oxidized redox current reporter.

9. The system of claim 1, wherein the redox current reporter comprises a molecule capable of undergoing reduction, thereby capturing electrons from the substrate and generating a reduced redox current reporter.

10. The system of claim 9, wherein the coreactant is capable of oxidizing the reduced redox current reporter.

11. The system of claim 1, w8herein the nucleic acid sequence is 17-27 nucleotides in length.

12. The system of claim 1 further comprising a common buffer in which the coreactant is contained.

13. The system of claim 1, wherein the coreactant is a reductant selected from the group consisting of oxalic acid ($C_2H_2O_4$), formic acid (HCOOH), ascorbic acid ($C_6H_8O_8$), a compound comprising an $Sn^{2+}$ ion or $Fe^{2+}$ ion, hydrazine, tris-(2-carboxyethyl) phosphine hydrochloride (TCEP), and any other reagent that will reduce an oxidized redox current reporter; or an oxidant selected from the group consisting of oxygen, hydrogen peroxide and other reactive oxygen species, a compound comprising an $Fe^{3+}$ ion, a compound comprising $ClO_4^-$, $BO_3^-$, $MnO_4^-$, $SO_5^{2-}$, $S_2O_8^{2-}$, $HSO_5^-$, $ClO_2^-$ or other halogen-containing anions, and any other reagent that will oxidize a reduced redox current reporter.

14. The system of claim 1, wherein the sensing unit lacks a redox enzyme.

15. The system of claim 1, wherein the system is configured for high throughput screening of a plurality of nucleic acids.

16. The system of claim 15, wherein the system comprises a plurality of sensing units, with a first sensor designed to detect a first nucleic acid and a second sensor designed to detect a second nucleic acid, wherein levels of expression of the first and second nucleic acids together signify the presence of a disease state.

17. A method of detecting a target nucleic acid in a sample, the method comprising:
   providing a sample comprising nucleic acids obtained from a subject or from a patient; and
   exposing the sample to the system of claim 1.

18. A method of making the system of claim 1, the method comprising
   (a) providing an electroconductive substrate;
   (b) immersing the substrate in a solution comprising sensing units for a time sufficient to allow the sensing units to self-assemble on the surface of the substrate, thereby generating a probe-functionalized substrate;
   (c) immersing the probe-functionalized substrate in a solution comprising passivating agents for a time sufficient to allow the agents to self-assemble on the surface of the substrate.

19. The method of claim 18, wherein the sensing unit comprises a sulfhydryl group, alkyne, or any functional group that provides precursors to bind to the electroconductive substrate; wherein the passivating agents comprise a sulfhydryl group or are an alkanethiol; or wherein the step of immersing the probe-functionalized substrate in a solution comprising inert thiol moieties further comprises heating and cooling the solution.

* * * * *